(12) United States Patent
Gumbrecht et al.

(10) Patent No.: US 7,838,261 B2
(45) Date of Patent: Nov. 23, 2010

(54) METHOD FOR PREVENTING CHEMICAL CROSSTALK IN ENZYME-LINKED REACTIONS, AND ASSOCIATED SYSTEM

(75) Inventors: Walter Gumbrecht, Herzogenaurach (DE); Rainer Hintsche, Berlin (DE); Konrad Mund, Uttenreuth (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1331 days.

(21) Appl. No.: 10/432,782

(22) PCT Filed: Nov. 26, 2001

(86) PCT No.: PCT/DE01/04437

§ 371 (c)(1),
(2), (4) Date: May 27, 2003

(87) PCT Pub. No.: WO02/41992

PCT Pub. Date: May 30, 2002

(65) Prior Publication Data

US 2004/0029203 A1 Feb. 12, 2004

(30) Foreign Application Priority Data

Nov. 24, 2000 (DE) ............................. 100 58 394

(51) Int. Cl.
*G01N 33/58* (2006.01)
(52) U.S. Cl. .................... 435/7.9; 506/11; 506/42; 506/43
(58) Field of Classification Search ............... None
See application file for complete search history.

(56) References Cited

U.S. PATENT DOCUMENTS 5,545,531 A    8/1996   Rava et al.
5,604,130 A *   2/1997   Warner et al. ............ 435/286.7
6,143,496 A   11/2000   Brown et al.

FOREIGN PATENT DOCUMENTS

WO    WO01/34842    5/2001

OTHER PUBLICATIONS

Proudnikov et al 1998 Anal. Biochem 259:34-41.*
Molekularbiologie der Zelle, 1997, 3A, p. 216, Methoden der Zellforschung, VCH Weinheim.
Paeschke et al., "A Stacked Multichannel Amperometric Detection System", Proceedings of the μTAS 94, Workshop, 1994, pp. 249-254, Kluver Academic Publishers.
Abstract of German Patent Publication No. DE19736641, published on Mar. 11, 1999.

* cited by examiner

*Primary Examiner*—Christopher Low
*Assistant Examiner*—Christopher M. Gross
(74) *Attorney, Agent, or Firm*—Staas & Halsey LLP

(57) ABSTRACT

A method for biochemical analysis uses a micro-reaction array with at least two reaction chambers for materials which react together chemically or biochemically. The reaction chambers are smaller than 1 μl, the reaction chambers are filled together by throughflow, the chemical or biochemical reactions of the substances retained therein then occurs in the individual isolated reaction chambers, thus preventing an interference between the reactions in the individual reaction chambers and the reaction products remain enclosed in the relevant reaction chambers. In the system the planar array has at least two reaction chambers for substances, whereby the reaction chambers are closed with the goal of preventing an exchange of substances.

13 Claims, 4 Drawing Sheets

METHOD FOR PREVENTING CHEMICAL CROSSTALK IN ENZYME-LINKED REACTIONS, AND ASSOCIATED SYSTEM

CROSS REFERENCE TO RELATED APPLICATIONS

This application is based on and hereby claims priority to PCT Application No. PCT/DE01/04437 filed on 26 Nov. 2001 and German Application No. 100 58 394.6 filed on 24 Nov. 2000, the contents of which are hereby incorporated by reference.

BACKGROUND OF THE INVENTION

The invention relates to a method for preventing chemical crosstalk in enzyme-linked reactions using a microreaction array having at least two reaction chambers for receiving substances which react chemically or biochemically with other substances. In addition, the invention also relates to a system for carrying out the method.

Combinatorial analysis and synthesis are nowadays in increasingly widespread use for the development of new active ingredients in the life sciences industry (pharmaceuticals), food technology, agro technology (crop science), in medical diagnostics and also to solve a very wide range of objectives in general biotechnology. To carry out these methods, what are known as microtitration plate techniques with reaction wells in an array structure are used, employing either 96 or even 384 wells for simultaneous reaction on an array surface of, for example, approx. 12×8 $cm^2$. The density of these arrays will increase further in future, which means that different types of chemical reactions have to take place in reaction chambers arranged ever closer together.

U.S. Pat. No. 6,143,496 A has disclosed a PCR (Polymerase Chain Reaction) method, in which, in an array having a multiplicity of reaction chambers, individual reactions take place next to one another at elevated temperatures. In this array, there are suitable ways to isolate specimen chambers, which can also be achieved, for example, by a displacement liquid. In particular, it is important to reduce the specimen volume or to prevent evaporation of water. The same problem in connection with a PCR method is discussed in WO 01/34842 A2, which claims an earlier priority but was not published before the priority date of the present application.

The situation is in principle different with what are known as DNA chips, as are known from various publications. The situation is taken to extremes, for example, with an array of different DNA probe molecules which are arranged at a spacing of only a few tens of micrometers and with a density of, for example, a few hundred positions per few $mm^2$ on a planar substrate, known as the DNA chip. If molecules which can move freely are involved in the analytical detection of, for example, unknown DNA, chemical crosstalk occurs with such dense arrays.

For a plurality of reasons, for example on account of the high specificity and the low detection limit, biochemical analysis often uses enzyme-linked detection methods. By way of example, what are known as ELISA (Enzyme-Linked ImmunoSorbent Assay) tests are in widespread use in medical diagnostics and in the research sector. (Literature reference c.f. B. Alberts et al. (eds.), Molekularbiologie der Zelle (Molecular biology of the Cell) (1997), 3rd edition, page 216, VCH Weinheim). Methods using enzyme markers in a known redox (re)cycling are also employed for applications in the field of the DNA chip (A.v.d.Berg, P. Bergveld (eds.) Proceedings of the µTAS '94 Workshop (1994), pp. 249 to 254, Kluwer Academic Publishers Dordrecht).

In all cases mentioned in the specialist literature, the enzyme is not free in the liquid phase of the arrangement, which is also known as an assay, but rather is bonded and therefore, as an "enzyme label" marks the primary substance to be detected. In this case, the bonding of the enzyme molecules to the substance to be detected is always stoichiometric. Amplification occurs in that the enzyme converts added substrate molecules at high speed. This conversion is quantified, for example, optically or electrochemically, depending on the substrate used and/or the product formed. For this purpose, irrespective of the method used, in particular the increase in concentration of the product P, i.e. the time-dependent function $dc(P)/dt$, is monitored.

If assays of this type are carried out in an array, as described in detail in the related art, reaction products which can move freely and are formed by the enzyme can also reach adjacent enzyme-free array positions, where they may simulate the presence of the enzyme label. This phenomenon is known as crosstalk, which leads to measurement errors and may therefore give false results.

SUMMARY OF THE INVENTION

Working on the basis of the above, it is one possible object of the invention to provide methods and associated systems which, compared to the related art, ensure increased reliability by avoiding crosstalk and thereby ruling out "false positive" results. An increased accuracy is intended to produce improvements in particular in the effectiveness of the measurements.

In the method, locally delimited reaction chambers are used as a first volume, and the reaction chambers can be connected to one another via a second volume, known as the supply volume, and in the individual reaction chambers chemical or biochemical reactions take place differentiated by species and/or quantitatively. Reactions differentiated by species are understood as meaning qualitatively different processes. In this case, equally, mass transfer between reaction chambers and the supply volume is permitted or prevented in one or both directions as required.

A significant advantage is that, despite the fact that the reaction chambers are closely adjacent, disruptive crosstalk, which may distort the measurement results, is rendered impossible, and the selectivity is thereby improved. Moreover, this also increases the detection sensitivity, i.e. the detection limit is shifted toward smaller quantities.

For practical realization of the detection sensitivity increase, it is appropriate for the change in substrate/product concentration over the course of time to be increased as far as possible. In the method, this is achieved by a targeted reduction in the reaction volume to significantly less than 1 µm, in particular to the region of 1 nanoliter (1 nl), and an associated increase in the substrate product concentration changes.

The systems are in each case arrays of more than two positions, and typically a few hundred positions, on a few square millimeters, preferably 1 to approx. 10 $mm^2$, arranged on a planar substrate. The array is in each case designed as an array of reaction chambers or reaction spaces and advantageously forms part of a vessel with a supply volume which is jointly accessible to the reaction chambers. A supply volume of this type can be produced, for example, by embedding the reaction chamber array in a flow cell, via which the overall fluid handling of the chemical/biochemical substances required for the detection or synthesis reaction can be performed.

In a first preferred embodiment, by pressing a mechanical device onto the substrate, the reaction chambers formed by the individual array positions can be separated from one another by an elastic membrane or layer which lies opposite the planar substrate in the flow cell and may be formed, for example, of silicone rubber, so that crosstalk is effectively prevented. A device of this type may, for example, be in the form of a cover, a ram or a sealing membrane, by which the cavities formed by the reaction chambers are closed off. Closing off the cavities also causes the volume of the liquid spaces above the individual array positions to be reduced, so that the change in concentration of the substrate/product which is initiated by the chemical/biochemical reactions is increased. Consequently, therefore, the detection sensitivity is also advantageously increased.

In another preferred embodiment, the same effect can be achieved by positioning a layer of barrier liquid on top. As soon as a suitable barrier liquid which cannot mix with the liquid in the reaction cavities fills the flow channel, the same effects are achieved as with the array cavities being closed up by a silicone ram. The barrier liquid is, for example, silicone oil. In an advantageous variant of this embodiment, the reaction chambers are filled with hydrogel, in order in this way to impart mechanical stability to the water-containing reaction chambers when the barrier liquid enters the flow channel. The hydrogel used may, for example, be polyacrylamide, which has the required properties with respect to silicone oil.

In a refinement, it is also possible to make use of different chemical solubility characteristics of the substances and materials involved. In this embodiment of the system too, the reaction chambers are advantageously filled with a hydrogel. Different solubility characteristics between hydrogel reaction chamber and a suitable liquid phase in the flow channel of the supply volume ensures that reaction starting materials from the liquid phase enter the hydrogel phase but reaction products can no longer leave the hydrogel phase. An example of a reaction starting product of this type is the enzyme substrate.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
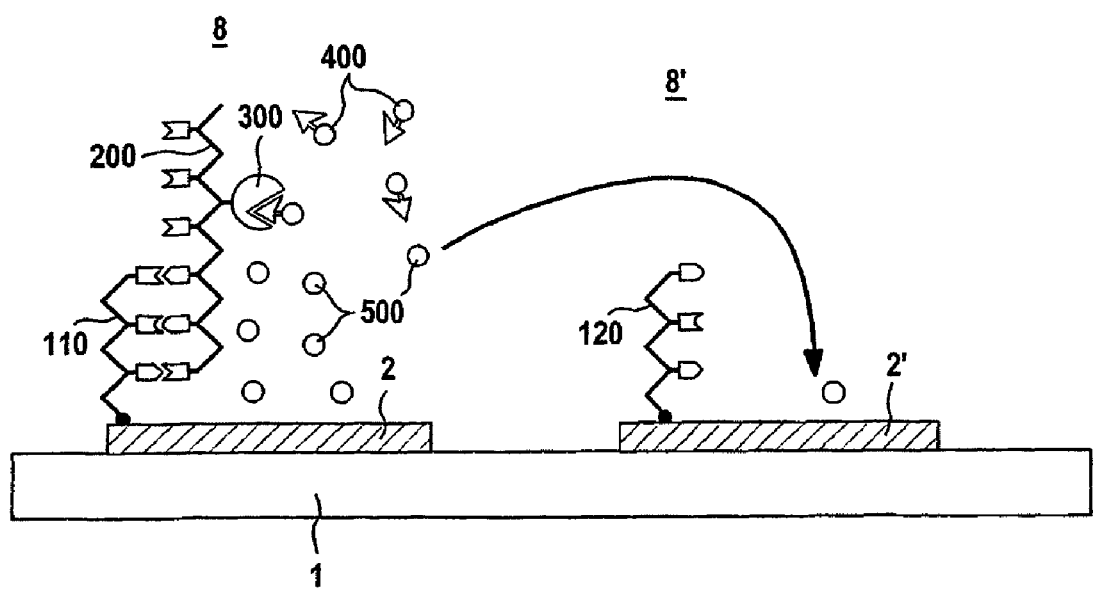
FIG. 1 diagrammatically depicts a measurement structure according to one aspect of the invention, illustrating the measuring method, on the one hand, and the disruptive crosstalk, on the other hand, FIG. 2 diagrammatically depicts, in three substeps, an example of a system for mechanically closing the cavities, FIG. 3 diagrammatically depicts, in the form of three substeps, a corresponding system for closing the cavities by barrier media, and FIG. 4 diagrammatically depicts, in the form of three substeps, a third system in which the cavities are closed off by utilizing different solubility characteristics of the media involved.

Reference will now be made in detail to the preferred embodiments of the present invention, examples of which are illustrated in the accompanying drawings, wherein like reference numerals refer to like elements throughout.

In the figures, parts which are identical or have a similar action are denoted by identical or corresponding reference numerals. The figures are in part described jointly in the text which follows.

In FIG. 1, 1 denotes a substrate with a planar surface which is formed, for example, by the crystallographic surface of a silicon chip. An array of optical/electrical detectors 2, 2', ... is produced on the substrate 1 at array positions 8, 8', ... and can be used to carry out bioanalytical tests using enzyme-linked reactions, for which purpose probe molecules, on the one hand, and analyte molecules, on the other hand, are used. On the array position 8, 8', ... there are different probe molecules 110, 120, ..., so that different analyte molecules can be detected on each specific array position.

In detail, in FIG. 1, for a method for bioanalytical testing, a first probe molecule is denoted by 110 at array position 8 and a second probe molecule is denoted by 120 at array position 8', an analyte molecule is denoted by 200 and an enzyme label is denoted by 300. By way of example, the probe molecule 110 reacts specifically with a complementary analyte module 200 and thereby immobilizes an enzyme label 300 in a position-specific manner in the array. An enzyme substrate 400 which is then added as starting material is converted into a product 500 by the catalytic effect of the enzyme label 300.

In FIG. 1, therefore, the analyte molecule 200 can react only with the probe molecule 110 but not with the probe molecule 120. The increase/decrease in substrate/product can be measured at each array position 8, 8', ... of the wafer 1 with the aid of the optical or electrical detector 2, 2', ... located there. In particular electrical detectors have metrological advantages.

In accordance with the related art, it is endeavored to keep the array positions 8, 8', ... and the distances between them as small as possible. A problem in the related art is that what is known as chemical crosstalk may occur between the individual positions 8, 8', ... This means that either enzyme substrate 400, which has been defined above as the starting material, or the reaction product 500 may move from a first array position 8 to a second array position 8'. If a neighboring position is reached, a false signal is generated, simulating a positive result. In practice, this is also referred to as a "false positive" signal.

Figure 2:
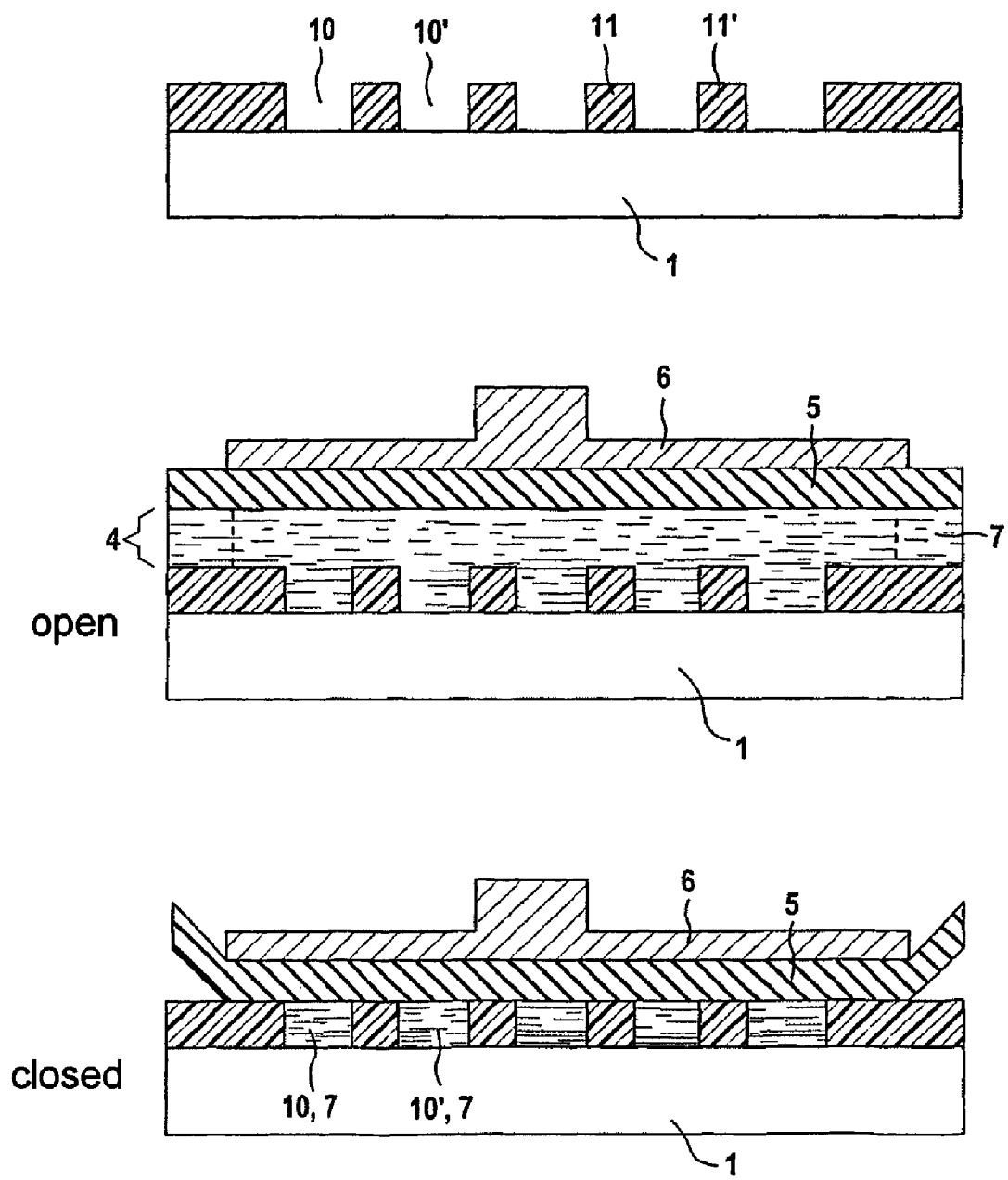
Figure 3:
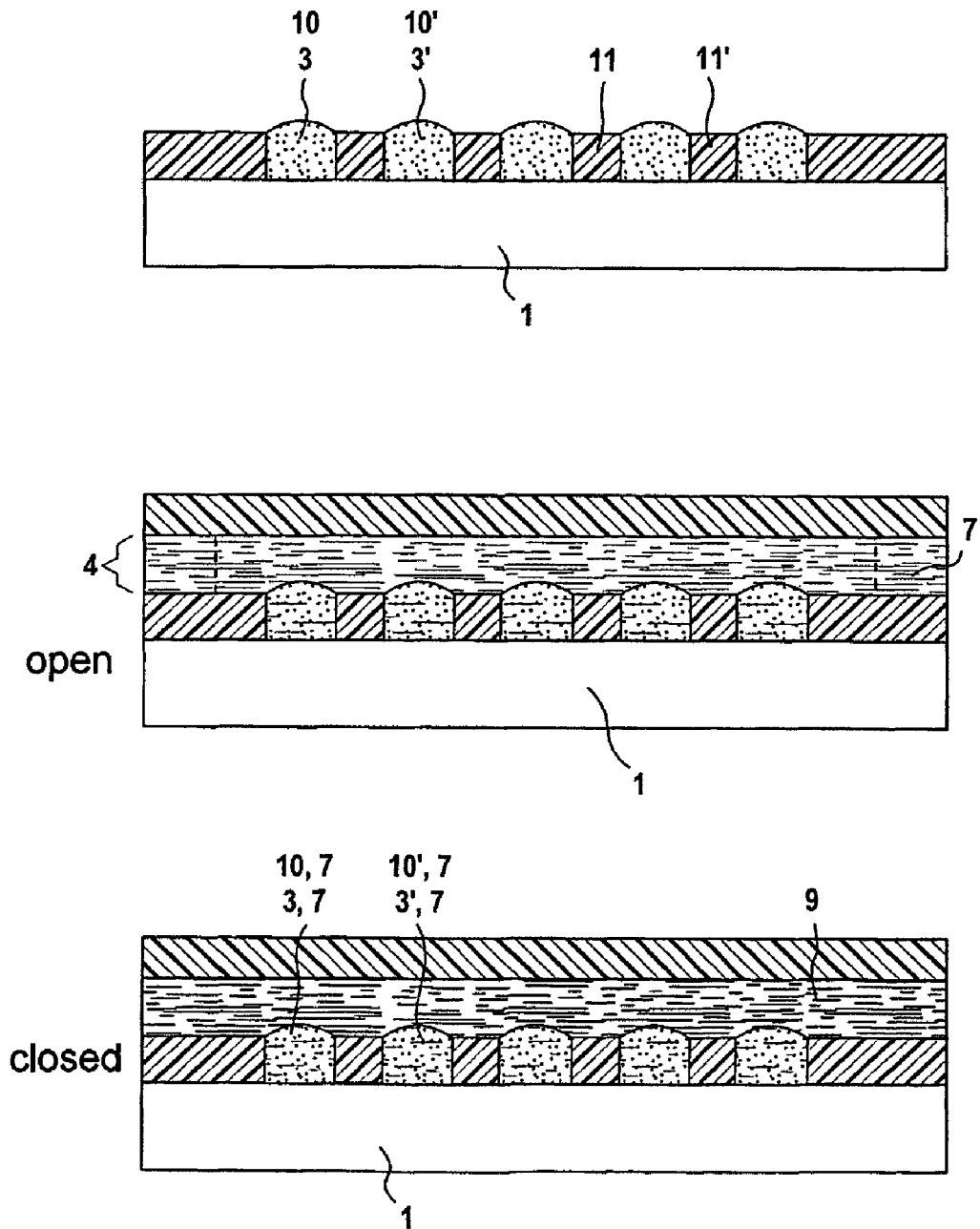
Figure 4:
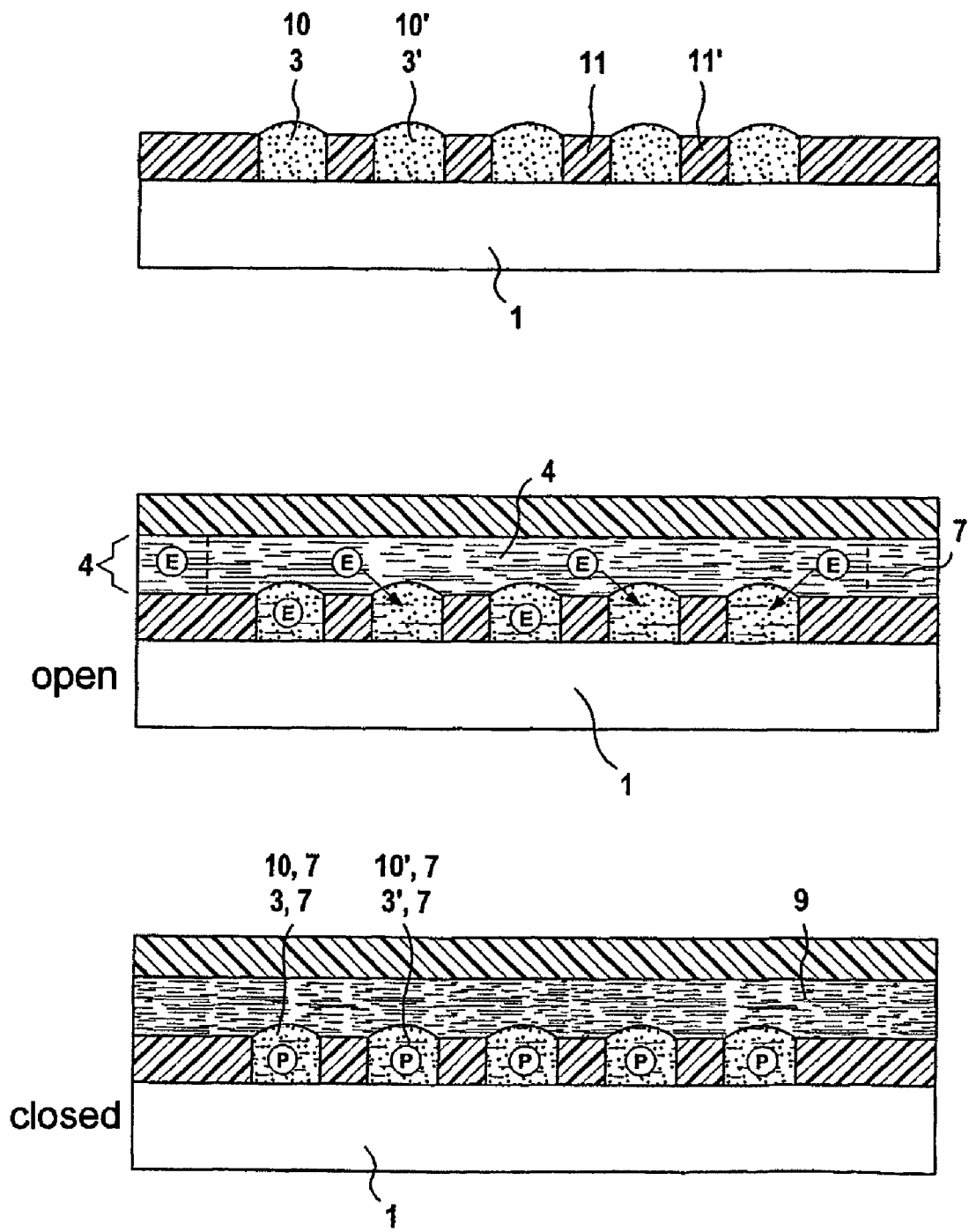

In FIGS. 2 to 4, for different alternatives individual reaction chambers 10,10', ... with an individual volume of in each case less than 1 μl are arranged in an array configuration. The reaction chambers 10,10', ... are operationally separated from one another.

FIG. 2 illustrates three substeps describing the actuation of a system in which the reaction chambers 10, 10', ... are separated by walls 11,11', ... The walls 11,11' can be produced in a particular geometric embodiment by photopatterned, circular polymer rings with an internal diameter of, for example, 150 μm, an external diameter of, for example, 180 μm and a height of, for example, 50,m. The reaction chambers 10, 10', ... are filled, for example, with reaction starting material, e.g. an enzyme substrate, dissolved in an electrolyte 7, the electrolyte 2 being supplied to the individual reaction chambers via a supply volume 4.

In FIG. 2, the reaction chambers 10,10', ... can be closed off by a housing top part 5 by a mechanical ram 6. In the open state, a supply volume 4 holding a liquid electrolyte is located above the cavities. In FIG. 2, the reaction spaces 10,10', ..., as chambers which are open when the housing top part 5 is removed, are filled with an electrolyte/starting material 7 flowing through them, the reservoir for the electrolyte 7 not being shown in detail in this figure. After the reaction cavities 10, 10', . . . have been filled with electrolyte/starting material 7, the housing top part 5, which may comprise, for example, a silicone membrane, is placed onto the walls 11, 11', . . . , which, as mentioned above, may be formed of polyimide, by the ram 6. In this way, the reaction spaces 10, 10', . . . are closed off, so that mass transfer is then prevented.

In FIG. 3, the lower region is of similar construction to that shown in FIG. 2. In a particular embodiment, which is not visible in the drawing presented in FIG. 3, the walls 11, 11', . . . may be specially produced by photopatterned, circular polymer rings with an internal diameter d (d=2r) of, for example, d=150 µm, an external diameter of, for example, D=180 µm, a height h of, for example, h=5 µm. The reaction cavities which result from dimensions of this type, with a filling volume of approximately 0.1 nl ($r^2\pi h$=(75 µm)$^2$*3.14*5 µm) are in this particular embodiment filled with a hydrogel 3 with a high capacity to take up water, e.g. polyacrylamide. Then, a probe DNA for specific DNA detection can be introduced in immobilized form into the hydrogel 3.

To carry out the assay, the reaction chambers 10, 10', . . . are once again supplied with buffer, reagents and ultimately enzyme substrate via the common supply volume 4. After the hydrogel 3 of each reaction chamber 10, 10' has been brought into equilibrium with buffer containing enzyme substrate and the enzymatic conversion has commenced, the supply volume 4 is flooded with a barrier liquid, e.g. silicone oil. The result of this is that the liquid above the reaction chambers is displaced by silicone oil. The hydrogel structure is responsible for the mechanical stability of the reaction chambers. Since enzyme product is insoluble in silicone oil, it is prevented from diffusing out of the hydrogel toward neighboring reaction chambers. Therefore, the reaction product can increase greatly in the reaction chambers without reaching the neighboring reaction chambers. Therefore, high sensitivity and high selectivity are equally present.

In both exemplary embodiments as shown in FIGS. 2 and 3, it is significant that the individual reaction cavities 10, 10', . . . are first of all filled with the electrolyte 7 passing through them from the supply volume 4 and then a material, for example a silicone oil 9, which forms phase boundaries with the electrolyte 7, is applied. The phase boundary ensures that mass transfer is then no longer possible and disruptive distortions are prevented.

In the specific variant of the embodiment shown in FIG. 3, the reaction chambers 10, 10', . . . are filled with hydrogel 3, e.g. polyacrylamide, in order, in this way to impart mechanical stability to the water-containing reaction chambers 10, 10', . . . when the barrier liquid 9, e.g. silicone oil, enters the flow channel.

In terms of its structure, FIG. 4 once again substantially corresponds to FIG. 2. In a corresponding way to FIG. 2 and FIG. 3, the reaction chambers 10, 10' are filled from the supply volume 4 by liquid passing through. In this case, however, the reaction starting materials, which are denoted here by E, have the ability, on account of their specific solubility characteristics, to penetrate into the electrolyte 7 located in the reaction chambers 10, 10', . . . after they have been filled.

In the system shown in FIG. 4, the reaction in the reaction chambers then takes place in the same way as has already been described above. On account of the specific solubility characteristics of the reaction product which forms and which is denoted here by P, however, mass discharge of P is not possible in the reaction. Therefore, the disruptive crosstalk is once again prevented. In this embodiment, too, in a corresponding way to FIG. 3, the reaction chambers are advantageously filled with a hydrogel 3.

The process described and the associated systems can be used particularly successfully in medical diagnostic and biotechnology. The prevention of crosstalk as a significant source of errors which is now achieved makes it possible to obtain more accurate results than has hitherto been possible.

The invention has been described in detail with particular reference to preferred embodiments therefore and examples, but it will be understood that variations and modifications can be effected within the spirit and scope of the invention.

The invention claimed is:

1. A method for inhibiting chemical crosstalk in enzyme-linked detection reactions, using a microreaction array with an array of reaction chambers for receiving substances which interact with one another, each reaction chamber having a respective volume, comprising:
   connecting the reaction chambers to one another via a supply volume so as to at permit mass transfer between the reaction chambers;
   selectively securing different enzyme labels in different reaction chambers such that different reaction chambers have a different enzyme label content;
   allowing enzyme-linked reactions to proceed differently in the reaction chambers based on the different enzyme label content, the enzyme-linked reactions producing a product; and
   closing the reaction chambers with a housing top part to inhibit chemical crosstalk, the housing top part disposed across openings in the reaction chambers to reduce the volume of the reaction chambers, and inhibit mass transfer of the product between the reaction chambers and the supply volume, in at least one direction,
   wherein the reaction chambers are mechanically opened and closed to connect the reaction chambers and inhibit mass transfer between the reaction chambers, respectively, and
   wherein the reaction chambers are closed off by the housing top part by means of a mechanical ram and opened by removing the housing top part.

2. The method as claimed in claim 1, wherein at a first time, mass transfer takes place between the reaction chambers and the supply volume, and, at a second time, mass transfer between the reaction chambers is inhibited.

3. The method as claimed in claim 1, wherein the reaction chambers and the supply volume contain different liquids having different solubility characteristics, and
   mass transfer in one direction is selectively inhibited by the different solubility characteristics.

4. The method as claimed in claim 1, wherein the reaction chambers are closed by displacement of the supply volume.

5. The method as claimed in claim 2, wherein the reaction chambers are connected by temporarily creating permeable phase boundaries between a substance located in the reaction chambers and a substance located in the supply volume.

6. The method as claimed in claim 4, wherein mass transfer is inhibited by displacement of the supply volume by a barrier medium.

7. The method as claimed in claim 6, wherein
   the supply volume is a liquid, and
   the supply volume is displaced by a gas.

8. The method as claimed in claim 6, wherein
   the supply volume is a liquid, and
   the supply volume is displaced by an immiscible liquid.

9. The method as claimed in claim 6, wherein
   the supply volume is a liquid, and
   the supply volume is displaced by silicone oil.

10. The method as claimed in claim 3, wherein
the reaction chambers contains a hydrogel layer,
starting materials for the reactions diffuse out of the supply volume into the hydrogel layer, and
the product does not diffuse out of the hydrogel layer.

11. The method as claimed in claim 1, wherein a combinatorial analysis or synthesis of substances takes place in individual reaction chambers.

12. The method as claimed in claim 1, wherein Redox recycling is performed with the enzyme-linked reactions.

13. The method as claimed in claim 2, wherein the reaction chambers are mechanically opened and closed by a physical block to connect the reaction chambers and inhibit mass transfer, respectively.

* * * * *